June 16, 1959 H. C. SWIM Plant Pat. 1,846
ROSE PLANT
Filed July 21, 1958
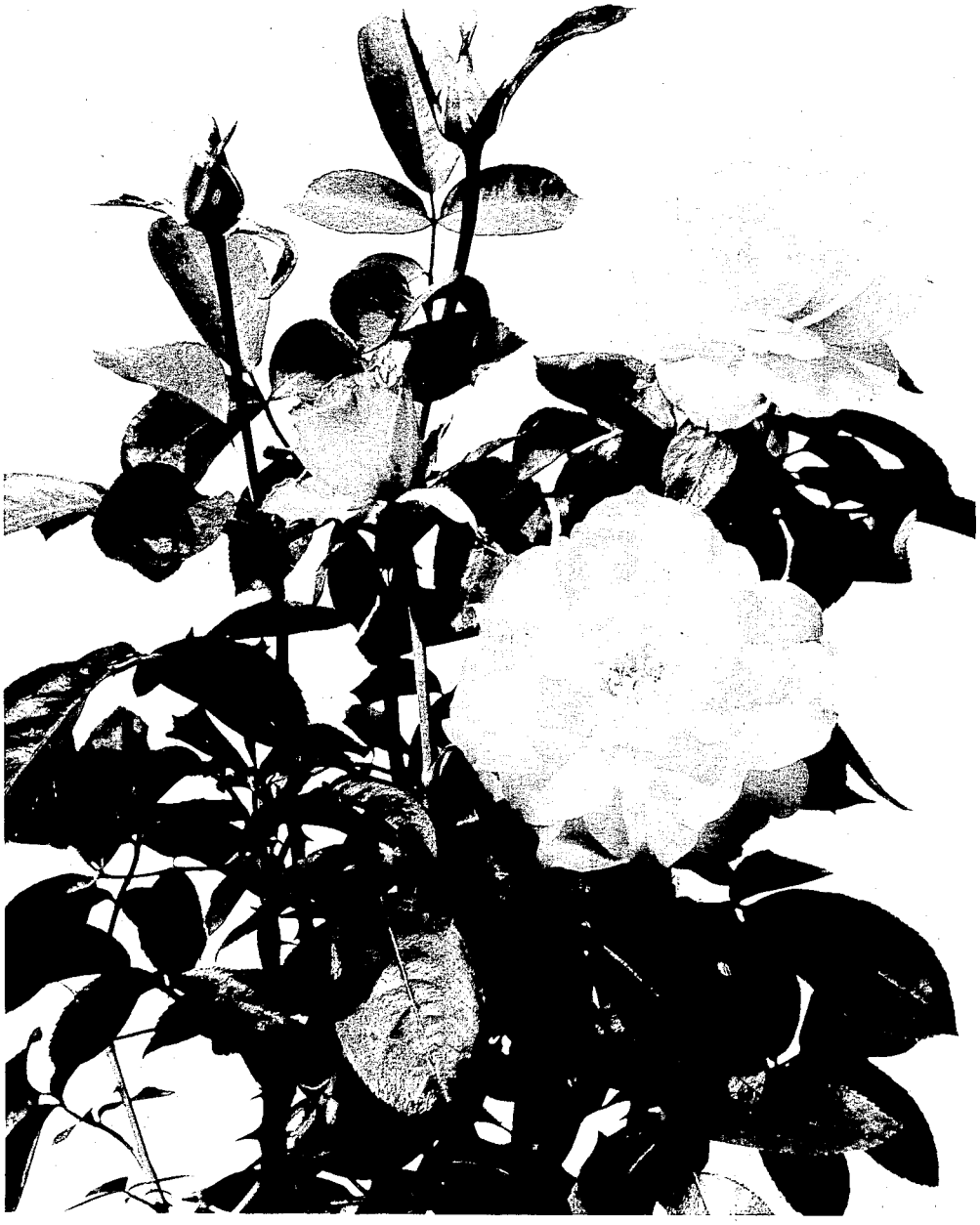
Inventor
H. C. Swim
By: Robb & Robb
Attorneys United States Patent Office Plant Pat. 1,846
Patented June 16, 1959

1,846

ROSE PLANT

Herbert C. Swim, Ontario, Calif., assignor to Armstrong Nurseries, Inc., Ontario, Calif., a corporation of California Application July 21, 1958, Serial No. 750,056
1 Claim. (Cl. 47—61)

The present invention relates to a new and distinct variety of rose plant of the class falling between the hybrid tea and floribunda classes, which was originated by me by planting on cultivated property of my assignee seed derived from the open-pollination of flowers of the variety known as "El Capitan" (Plant Patent No. 1,796).

The primary objective sought to be achieved by me in the planting of the seed aforesaid was to produce a new rose variety generally similar to "El Capitan" in both plant and flower characteristics, but in which the flowers are of a different color, falling in a range between pink and red, and particularly of a more brilliant color of the orange-scarlet type. This objective was fully achieved, along with other desirable improvements, as evidenced by the following unique combination of characteristics which are outstanding in the new variety and distinguish it from its parent, as well as from all other varieties of which I am aware:

(1) Vigorous, bushy and upright habits of plant growth;

(2) Attractive, glossy foliage ranging in size from medium to large;

(3) A habit of bearing flowers sometimes singly and sometimes in few-flowered clusters, with the flowers borne on stems of medium length;

(4) A floriferousness similar to that of the variety of "El Capitan";

(5) Attractive, well-formed, high-centered, double flowers of medium petalage;

(6) A flower size ranging from medium to large, similar to that of the variety "El Capitan";

(7) A brilliant and distinctive general color tonality of the flowers corresponding to near Orient Red; and (8) Better-than-average petal substance similar to that of the variety "El Capitan," with attendant long-lasting qualities of the flowers.

In comparison with its parent variety "El Capitan," the plant of my new variety is usually somewhat less vigorous in habit, and the flowers are near Orient Red in general color tonality, and thus more orange-scarlet than those of the parent which have a color between Cherry and Rose Red.

Asexual reproduction of my new variety by budding, as performed at Ontario, Carlifornia, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson) and Robert Ridgway's Color Standards and Nomenclature (hereinafter abbreviated as "Ridgway"), except where general color terms of ordinary dictionary significance are obvious:

Type: Bush; outdoor; seedling; for cut flowers and for garden decoration.
Class: Between hybrid tea and floribunda.
Breeding: Seedling.

*Seed parent.*—"El Capitan."
*Pollen parent.*—Unknown.
Propagation: Holds its distinguishing characteristics through succeeding propagations by budding.

*Flower*

Locality where grown and observed: Ontario, California.
Flowers borne: Sometimes singly to stem, and sometimes in few-flowered, irregular clusters of 3 to 5 or more flowers; on stems of medium length and normal strength.
Quantity of bloom: Abundant, outdoors.
Continuity: Nearly continuous during growing season.
Fragrance: From none to slight.
Bud:
*Peduncle.*—Average length; average caliper; erect; usually smooth; with few stipitate glands and few prickles. Color—near Prussian Red, Plate XXVII (Ridgway) on side exposed to the sun.
*Before calyx breaks.*—Size—from small to medium. Form—from moderately short to medium length; ovoid; with foliaceous appendages on the surface of the bud; usually with slender foliaceous parts extending beyond the tip of the bud equal to ½ or more of its length.
*As calyx breaks.*—Color—near Chrysanthemum Crimson, Plate 824, page 169 (Wilson).
*Sepals.*—Inner surface—lined with fine, woolly tomentum; margins of alternate sepals lined with fine, woolly tomentum; others lined with stipitate glands. Outer surface—moderately smooth.
*As first petal opens.*—Size—from small to average size.—Form—from short to medium length; ovoid. Color: outside—between Blood Red, Plate 820/3, page 166 (Wilson) and Currant Red, Plate 821/2, page 167 (Wilson), and with small area at base of petal near attachment near Uranium Green, Plate 63/2, page 63 (Wilson); inside—between Orient Red, Plate 819/3, page 165 (Wilson) and Blood Red, Plate 820/2, page 166 (Wilson), and with small area at base of petal near attachment near Uranium Green, Plate 63/2, page 63 (Wilson).
*Opening.*—Opens up well; is not retarded from opening by cold, hot, wet or dry weather.
Bloom:
*Size (when fully open).*—From average size to large; from 3½ inches to 4½ inches.
*Petalage.*—Double; from 20 to 28 petals, plus from 4 to 8 petaloids; arranged regularly.
*Form.*—High-centered and globular at first, but becoming cupped to high-centered; petals at first being somewhat loosely cupped, with tips slightly reflexed outward but later becoming more loosely cupped at maturity, with tips reflexed outward.
Petals:
*Texture.*—Thick; leathery. Inside—slightly velvety. Outside—satiny.
*Shape.*—Outside—broadly obovate, with apex flat. Intermediate—obovate, with apex from rounded to flat. Inside—narrowly obovate, with apex rounded.

This description of a newly opened flower was made from a rose grown outdoors in the month of August at Ontario, California:

*Color.*—Outer petal: outside surface—near Currant Red, Plate 821/3, page 167 (Wilson); occasional petals have lighter colored vegetative streaks through centers; inside surface—between Cherry, Plate 722/1, page 157 (Wilson) and Orient Red, Plate 819/3, page 165 (Wilson); occasional petals have lighter colored vegetative streaks through centers. Intermediate petal: outside surface—near Currant Red, Plate 821/3, page 167 (Wilson); occasional petals have lighter colored vegetative streaks through centers; inside surface—near Orient Red, Plate 819/1, page 165 (Wilson); occasional petals have lighter colored vegetative streaks through centers. Inner petal: outside surface—near Cherry, Plate 722, page 157 (Wilson); occasional petals have lighter colored vegetative streaks through centers; inside surface—near Orient Red, Plate 819, page 165 (Wilson); occasional petals have lighter colored vegetative streaks through centers.

This description was made from a rose that was open for 3 days outdoors in the month of August at Ontario, California:

*Color.*—Outer petal: outside surface—near Cherry Plate 722/2, page 157 (Wilson); occasional petals have lighter colored vegetative streaks through centers; inside surface—between Claret Rose, Plate 021, page 109 (Wilson) and Orient Red, Plate 819/3, page 165 (Wilson); occasional petals have lighter colored vegetative streaks through centers. Inner petal: outside surface—near Cherry, Plate 722/3, page 157 (Wilson); occasional petals have lighter colored vegetative streaks through centers; inside surface—between Claret Rose, Plate 021, page 109 (Wilson) and Orient Red, Plate 819/3, page 165 (Wilson); occasional petals have lighter colored vegetative streaks through centers.

*General color effect.*—Newly opened flower—between Orient Red, Plate 819/1, page 165 (Wilson) and Orient Red, Plate 819/2, page 165 (Wilson). 3-days open—between Claret Rose, Plate 021, page 109 (Wilson) and Orient Red, Plate 819/3, page 165 (Wilson).

*Behavior.*—Drop off cleanly; not particularly affected by cold, hot, wet or dry weather.

*Flower longevity.*—On bush in garden—4 or 5 days in August. Cut roses grown outdoors and kept at living-room temperatures—5 or 6 days in August.

*Reproductive organs*

Stamens: Average number; arranged regularly about pistils; a few mixed with petaloids.

Filaments: From medium length to long; from 5 to 12 mm. in length; most with anthers. Color—near Carmine, Plate 21/3, page 21 (Wilson).

Anthers: Medium size; all open approximately at once. Color: upper side—margins near Chinese Yellow, Plate 606/2, page 68 (Wilson), with remainder near Empire Yellow, Plate 603/3, page 66 (Wilson); under side—margins near Chinese Yellow, Plate 606/2, page 68 (Wilson), with remainder near Empire Yellow, Plate 603/3, page 66 (Wilson).

Pollen: From moderate to abundant. Color—near Indian Yellow, Plate 6/2, page 6 (Wilson).

Pistils: Many; approximately 85 in number.

Styles: Moderately even; average length; from 5 to 8 mm. in length; average caliper; bunched. Color—upper ⅓ of style near Pansy Purple, Plate 928/3, page 177 (Wilson), with remainder near China Rose, Plate 024, page 111 (Wilson).

Stigma: Color near Spinel Red, Plate 0023/1, page 189 (Wilson).

Ovaries: Usually all enclosed in calyx.

Hips: None observed.

Sepals: Permanent; medium length; curled and recurved. Color: inside—near Corydalis Green, Plate XLI (Ridgway); outside—near Biscay Green, Plate XVII (Ridgway), overlaid with near Dark Vinaceous Brown, Plate XXXIX (Ridgway).

Seeds: None observed.

*Plant*

Foliage:

*Leaves.*—Compound of usually 3 to 5 leaflets; abundant; from medium size to large; leathery; glossy.

*Leaflets.*—Shape—ovate, with apex acute. Base—round. Margin—simply serrate.

*Color.*—Mature: upper surface—near Deep Dull Yellow Green (1), Plate XXXII (Ridgway); under surface—between Light Grape Green, Plate XLI (Ridgway) and Mytho Green, Plate XLI (Ridgway). Young: upper surface—near Oil Green, Plate V (Ridgway), overlaid with varying degrees of near Indian Red, Plate XXVII (Ridgway); under surface—near Citrine Drab, Plate XL (Ridgway), overlaid with varying degrees of near Indian Red, Plate XXVII (Ridgway).

*Rachis (the supporting stem of the compound leaf).*—Average size. Upper side—grooved; with some stipitate glands on edges. Under side—moderately smooth; with stipitate glands and sometimes 2 or 3 prickles.

*Stipules.*—Medium length; medium width; with short to medium length points turning out at an angle of less than 45°.

*Disease resistance.*—Better-than-average resistance to mildew, as compared with other varieties grown under comparable cultural conditions at Ontario, California.

Growth:

*Habit.*—Bushy; upright, much-branched.

*Growth.*—Vigorous.

*Canes.*—From medium to heavy caliper.

*Main stems.*—Color—near Rainette Green, Plate XXXI (Ridgway). Large prickles—several; moderately short; hooked slightly downward; with long, narrow base; color—near Verona Brown, Plate XXIX (Ridgway). Small prickles—few; color—near Verona Brown, Plate XXIX (Ridgway). Hairs—none.

*Branches.*—Color—near Deep Chrysolite Green, Plate XXXI (Ridgway). Large prickles—several; moderately short; hooked slightly downward; with long, narrow base; color—near Walnut Brown, Plate XXVIII (Ridgway). Small prickles—few; color—near Walnut Brown, Plate XXVIII (Ridgway). Hairs—none.

*New shoots.*—Color—near Ocher Red, Plate XXVII (Ridgway). Large prickles—few; moderately short; hooked slightly downward; with long, narrow base; color—near Indian Red, Plate XXVII (Ridgway). Small prickles—few; color—near Indian Red, Plate XXVII (Ridgway). Hairs—none.

I claim:

A new and distinct variety of rose plant of the class falling between the hybrid tea and floribunda classes, substantially as herein shown and described, characterized particularly as to novelty by its unique combination of vigorous, bushy and upright habits of plant growth, attractive, glossy foliage ranging in size from medium to large, a habit of bearing flowers sometimes singly and sometimes in few-flowered clusters on stems of medium length, a floriferousness similar to that of the variety "El Capitan" (Plant Patent No. 1,796), attractive, well-formed, high-centered, double flowers of medium petalage, a flower size ranging from medium to large, similar to that of the variety "El Capitan," a brilliant and distinctive general color tonality of the flowers corresponding to near Orient Red, and better-than-average petal substance similar to that of the variety "El Capitan," with attendant long-lasting qualities of the flowers.

No references cited.